（12）United States Patent
Otomaru et al.

(10) Patent No.: US 11,457,877 B2
(45) Date of Patent: Oct. 4, 2022

(54) IMAGE PROCESSING APPARATUS, IMAGE PROCESSING METHOD, AND NON-TRANSITORY COMPUTER-READABLE MEDIUM

(71) Applicant: CANON KABUSHIKI KAISHA, Tokyo (JP)

(72) Inventors: Itaru Otomaru, Kawasaki (JP); Takaaki Endo, Urayasu (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 25 days.

(21) Appl. No.: 16/858,362

(22) Filed: Apr. 24, 2020

(65) Prior Publication Data

US 2020/0253566 A1  Aug. 13, 2020

Related U.S. Application Data

(63) Continuation of application No. PCT/JP2018/039304, filed on Oct. 23, 2018.

(30) Foreign Application Priority Data

Oct. 31, 2017  (JP) .............................. JP2017-210832

(51) Int. Cl.
*G06K 9/00* (2022.01)
*A61B 6/03* (2006.01)
(Continued)

(52) U.S. Cl.
CPC .................. *A61B 6/03* (2013.01); *G06T 7/13* (2017.01); *G06T 11/008* (2013.01); *G06T 2207/10081* (2013.01)

(58) Field of Classification Search
CPC ........................................................ A61B 6/03
See application file for complete search history.

(56) References Cited

U.S. PATENT DOCUMENTS 11,311,259 B2 * 4/2022 Otomaru ............... G06T 11/008
2007/0172104 A1 * 7/2007 Nishide ................. G06T 11/008
382/131

(Continued)

FOREIGN PATENT DOCUMENTS

JP    2004-357866 A    12/2004
JP    2005-296052 A    10/2005
(Continued)

OTHER PUBLICATIONS

Hiroshi Fujita; "Present and Future of Breast Imaging Technology: Image Processing Techniques in Mammography;" Journal of the Society of Photography and Imaging of Japan, vol. 69, No. 1, 16-22, 2006.

(Continued)

*Primary Examiner* — Hadi Akhavannik
(74) *Attorney, Agent, or Firm* — Canon U.S.A., Inc. IP Division

(57) ABSTRACT

An image processing apparatus includes projection unit configured to generate first two-dimensional image data by applying a projection process to three-dimensional image data, acquisition unit configured to acquire a second parameter related to image processing based on a first parameter related to the projection process, and image processing unit configured to generate second two-dimensional image data by applying the image processing to the first two-dimensional image data using the at least one or more second parameters.

26 Claims, 9 Drawing Sheets

(51) Int. Cl.
*G06T 7/13* (2017.01)
*G06T 11/00* (2006.01)

(56) References Cited

U.S. PATENT DOCUMENTS

| | | | | |
|---|---|---|---|---|
| 2007/0206008 | A1* | 9/2007 | Kaufman | G06T 15/06 345/427 |
| 2008/0037847 | A1* | 2/2008 | Avinash | G06T 7/194 382/131 |
| 2008/0074422 | A1* | 3/2008 | Dekel | G06T 15/08 345/427 |
| 2010/0194750 | A1* | 8/2010 | Mielekamp | G06T 19/00 345/592 |
| 2013/0222383 | A1* | 8/2013 | Taniguchi | A61B 6/466 345/424 |
| 2014/0369466 | A1* | 12/2014 | Yamashita | A61B 6/465 378/42 |
| 2016/0035102 | A1* | 2/2016 | Jerebko | G06T 7/155 382/131 |
| 2016/0343117 | A1* | 11/2016 | Schultz | G06T 5/20 |

FOREIGN PATENT DOCUMENTS

| | | |
|---|---|---|
| JP | 2009-6086 A | 1/2009 |
| JP | 2014-30693 A | 2/2014 |
| JP | 2016-77795 A | 5/2016 |
| WO | 2006/033377 A1 | 3/2006 |
| WO | 2007/033377 A2 | 3/2007 |
| WO | 2014/200019 A1 | 12/2014 |

OTHER PUBLICATIONS

Masayuki, Nakazawa et al.; "Dynamic Range Compression Technique for Digital X-Ray Images;" Konica Technical Report, vol. 9, 35-40, 1996.

* cited by examiner

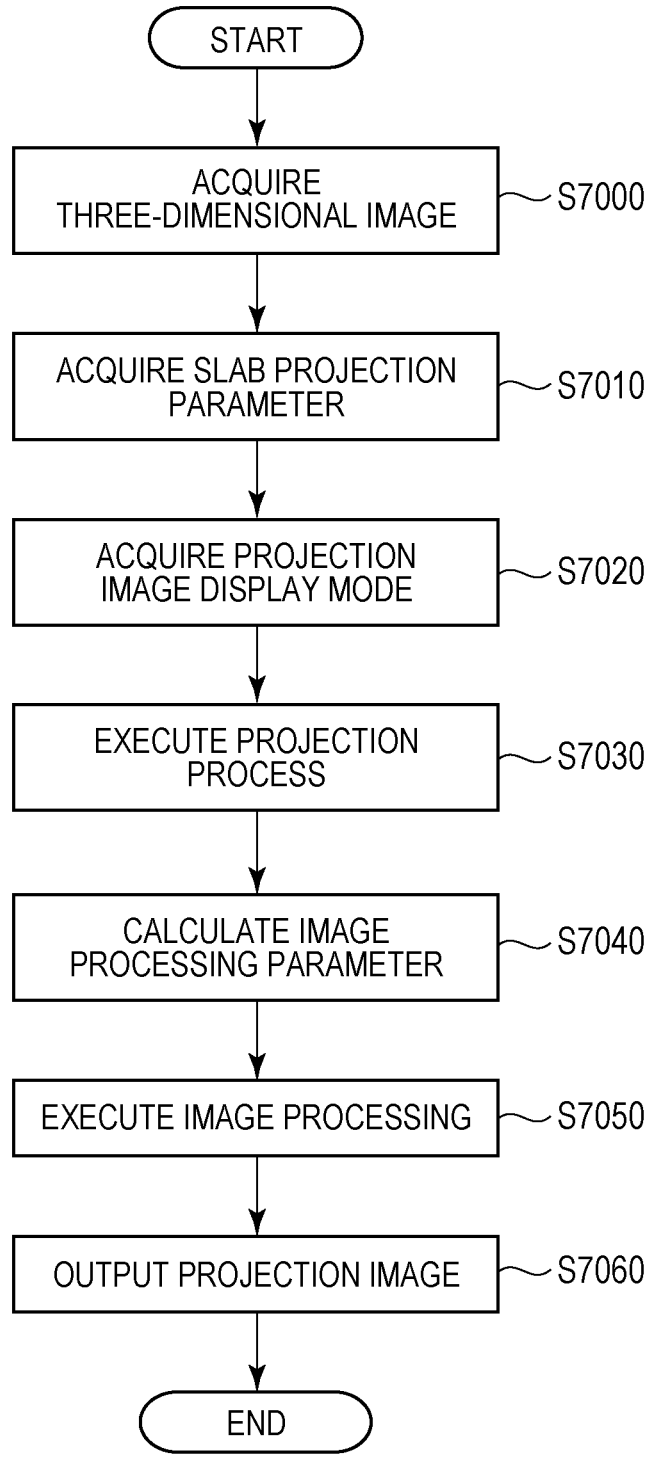

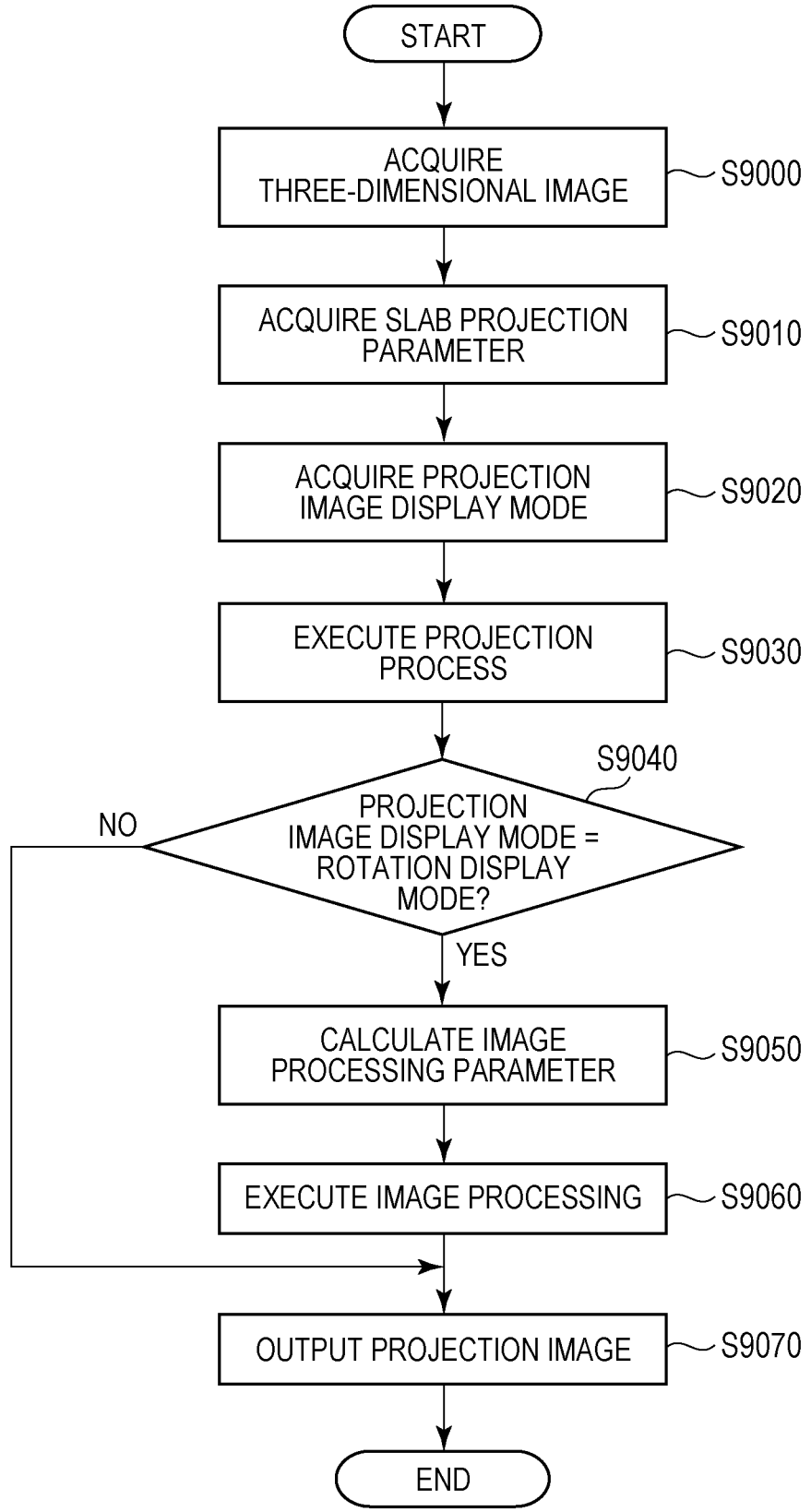

IMAGE PROCESSING APPARATUS, IMAGE PROCESSING METHOD, AND NON-TRANSITORY COMPUTER-READABLE MEDIUM

CROSS-REFERENCE TO RELATED APPLICATIONS

This application is a Continuation of International Patent Application No. PCT/JP2018/039304, filed Oct. 23, 2018, which claims the benefit of Japanese Patent Application No. 2017-210832, filed Oct. 31, 2017, both of which are hereby incorporated by reference herein in their entirety.

BACKGROUND OF THE INVENTION

Field of the Invention

The present invention relates to an image processing apparatus, an image processing method, and a non-transitory computer-readable medium.

Description of the Related Art

In a medical field, imaging apparatuses (modalities) capable of acquiring high-definition three-dimensional image data of a subject, such as a three-dimensional CT (Computed Tomography) imaging apparatus, an MRI (Magnetic Resonance Imaging) apparatus and the like have been developed. Compared to two-dimensional medical image data represented by a conventional simple X-ray image, three-dimensional image data includes a greater number of images to be interpreted. Therefore, there is a need for an image display method that allows a three-dimensional structure of a subject to be grasped at a glance without significantly increasing an interpretation time.

As a popular display method for grasping a three-dimensional structure of a subject from one two-dimensional image, various projection display techniques are known. It is known to use project three-dimensional image data into a two-dimensional image by one of various projection methods such as a maximum intensity projection, volume rendering, or the like and display a resultant projection image. For example, to observe a region of interest such as a lesion in the projection display, a "slab projection" may be performed so as to limit the projection range to a certain thickness (a slab thickness). Japanese Patent Application Laid-Open No. 2014-30693 discloses a technique for, in the slab projection, reducing a calculation time required for a projection calculation by performing a pre-calculation. Japanese Patent Application Laid-Open No. 2016-77795 discloses a technique for improving the visibility in image interpretation by performing image processing on a projection image.

However, the techniques disclosed in Japanese Patent Application Laid-Open No. 2014-30693 and Japanese Patent Application Laid-Open No. 2016-77795 have a problem that a reduction in the visibility of a region of interest may occur when the slab projection is performed.

SUMMARY OF THE INVENTION

It is an object of the present invention to make it possible to display a region of interest in projecting three-dimensional image data into a two-dimensional image such that high visibility is achieved for the region of interest.

It is to be noted that in addition to the above object, it is another of the present invention to provide an effect unachievable by conventional techniques by providing various embodiments of the present invention.

The image processing apparatus according to an aspect of the present disclosure has the following configuration including projection unit configured to generate first two-dimensional image data by applying a projection process to three-dimensional image data, acquisition unit configured to acquire a second parameter used in image processing based on the first parameter of the projection process, and image processing unit configured to generate second two-dimensional image data by applying the image processing to the first two-dimensional image data using the second parameter.

Further features of the present invention will become apparent from the following description of exemplary embodiments with reference to the attached drawings.

BRIEF DESCRIPTION OF THE DRAWINGS

FIG. 7 is a flowchart illustrating an overall processing procedure according to a second embodiment.

FIG. 9 is a flowchart illustrating an overall processing procedure according to a third modification of the second embodiment.

DESCRIPTION OF THE EMBODIMENTS

Figure 1:
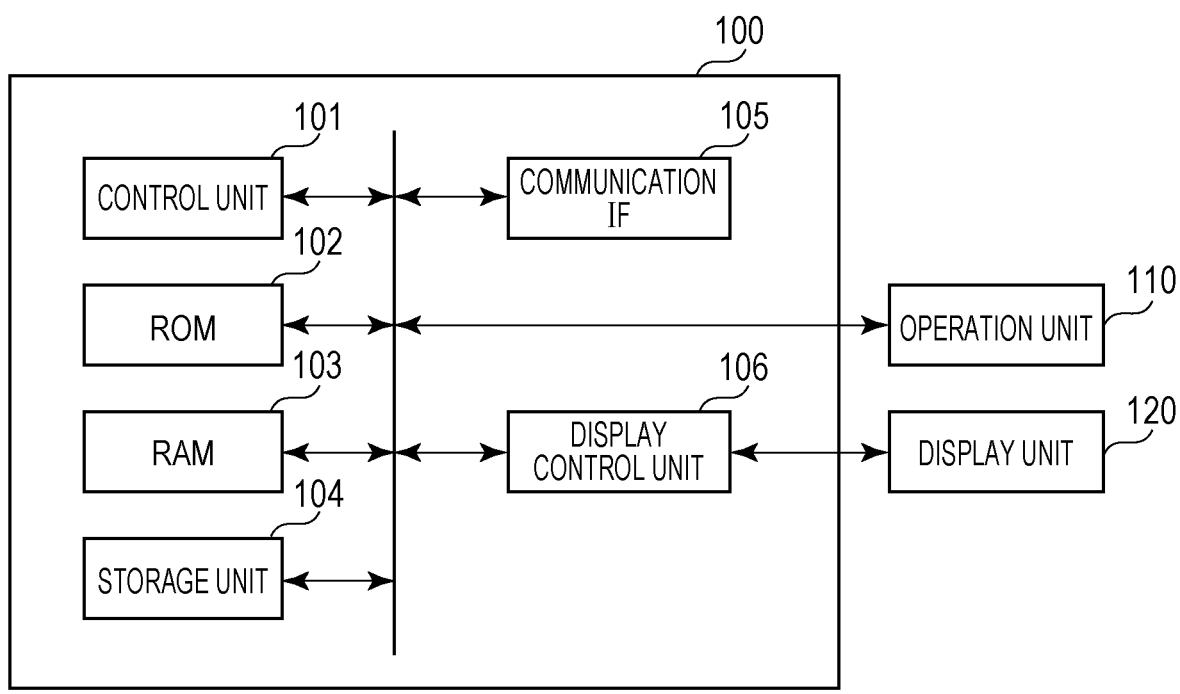
FIG. 1 is a diagram illustrating a hardware configuration of an image processing apparatuses according to a first embodiment and that according to a second embodiment.

Preferred embodiments of the present invention are described in detail below with reference to the accompanying drawings. Note that the scope of the invention is not limited to the illustrated examples.

First Embodiment

In a first embodiment, an image processing apparatus, a visibility of a region of interest is improved by adjusting a parameter of image processing applied to a projection image depending on a slab thickness in two-dimensional image projection processing. The present embodiment is described below by way of example for a case in which processing is performed on three-dimensional CT image data obtained by imaging a breast region using an X-ray CT apparatus (hereinafter, referred to as a breast CT image). Note that it is assumed that the region of interest in a breast CT image refers to a tumor region.

Although the present invention is described by way of example for a case in which a subject is imaged by the X-ray CT apparatus, apparatuses other than the X-ray CT apparatus may be used in the present invention. For example, a wide variety of modalities such as an MRI apparatus, a three-dimensional ultrasonic imaging apparatus, a photoacoustic tomography apparatus, a PET/SPECT (Position Emission Tomography/Single Phonon Emission Computer Tomography) apparatus, an OCT (Optical Coherence Tomography) apparatus, and the like may be employed.

A problem that is to be solved by embodiments will be specifically described below. In interpretation of a breast CT image, two-dimensional projection image data is calculated and displayed using a total sum projection (Ray Summation projection method, hereinafter, referred to as RaySum projection), which is one of known projection techniques. RaySum projection is a projection method in which, when the density value of a pixel on a projection image is calculated, the sum of all density values on a projection path leading to the pixel is assigned as the density value of the pixel. By using the RaySum projection, it is possible to observe a gradation necessary in an image interpretation. For example, it is possible to observe a contour of a region of interest such as a tumor region, and a manner in which surrounding tissue is drawn into the tumor. On the other hand, in a case where the slab thickness is greater than a particular value (for example, 5 mm or more for breast CT images), the contrast and the sharpness of an image decrease (that is, an increase in blur occurs) with increasing slab thickness, which results in an increase in difficulty of observing the tumor region.

To handle the above situation, the present embodiment employs an approach of improving sharpness of a region of interest by applying a sharpening process to the projection image. As the sharpening process, a multi-resolution sharpening process is used, which is a known method disclosed in "Present and Future of Breast Imaging Technology: Image Processing Techniques in Mammography" (Fujita, Journal of the Society of Photography and Imaging of Japan, Vol. 69, No. 1, 16-22, 2006). By performing the sharpening process, even when the slab thickness is set to a large value, it is possible to obtain a sharp image in which the outline and the linear structure are emphasized. On the other hand, when no projection is performed (when the slab thickness is 0, that is, when an image slice is displayed as it is) or when the slab thickness is small, if the sharpening process is performed, the resultant image is unnatural and includes emphasized noise. In view of the above, in the present embodiment, in a case where no projection is per formed or the slab thickness is smaller than a particular value, the degree of an effect of the sharpening process is reduced (or the sharpening process is not performed). In a case where the slab thickness is larger than the particular value, the effect of the sharpening process is enhanced thereby handling the situation described above.

Configurations and processes of the present embodiment are described with reference to FIGS. 1 to 4.

FIG. 1 illustrates an example of a hardware configuration of the image processing apparatus 100 according to the present embodiment. It should be noted that the hardware configuration of the image processing apparatus shown in FIG. 1 is merely an example, and the hardware configuration is not limited to this example.

The image processing apparatus 100 includes a control unit 101, a read only memory (ROM) 102, a random access memory (RAM) 103, a storage unit 104, a communication interface (communication IF) 105, and a display control unit 106. These hardware units are connected to a system bus. An operation unit 110 and a display unit 120 are connected to the image processing apparatus 100. Note that the configuration includes at least one each of the hardware units described above.

The control unit 101 is, for example, a processor such as a CPU (Central Processing Unit), and generally controls each hardware unit connected to the system bus. The ROM 102 is realized using a nonvolatile memory or the like. Various programs are stored in the ROM 102. The RAM 103 is a hardware unit realized using a volatile memory or the like. The RAM 103 is a hardware unit used by the control unit 101 as a main memory, a work area, or the like, for temporarily storing various kinds of information as data. The storage unit 104 is, for example, an HDD (Hard Disk Drive), an SSD (Solid State Drive), or the like. The communication IF 105 is, for example, a LAN (Local Area Network) card or the like, and realizes communication between an external apparatus (for example, a data server) and the image processing apparatus 100 via a network. The display control unit 106 is a control unit that performs control such that the display unit 120 displays various kinds of information. The display control unit 106 corresponds to, for example, a graphic controller (a GPU, or the like). Instead of providing the display control unit 106, the function of the display control unit 106 may be incorporated in the control unit 101.

The operation unit 110 is an apparatus for inputting an instruction given by a user to the image processing apparatus 100. The operation unit 110 includes a keyboard, a mouse, a touch panel, and/or the like. The display unit 120 is a display apparatus (for example, a liquid crystal display apparatus the like) for displaying various kinds of information under the control of the display control unit 106.

In the present invention, various programs and the like used by the image processing apparatus 100 to execute various processes described below are stored in the storage unit 104 and loaded into the RAM 103 as required and the control unit 101 executes the loaded programs. Furthermore, definition files and various information tables used by the program according to the present invention are stored in the storage unit 104.

Figure 2:
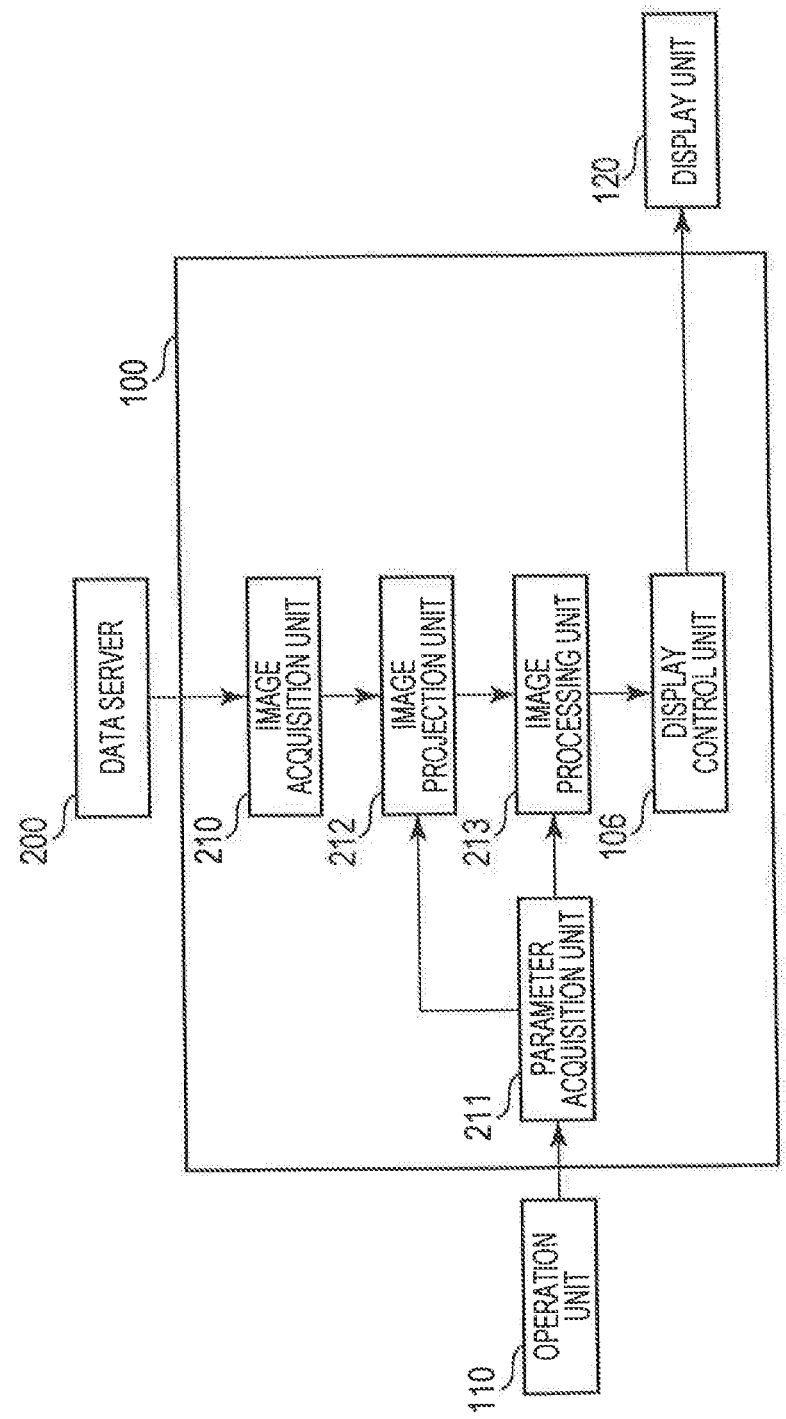
FIG. 2 is a diagram illustrating a functional configuration of the image processing apparatuses according to the first embodiment and that according to the second embodiment.

FIG. 2 illustrates an example of a system configuration of an image processing system and a functional configuration of the image processing apparatus 100 according to the present embodiment. It should be noted that the configurations shown in FIG. 2 are merely examples, and the present invention is not limited thereto. In the present embodiment, as shown in FIG. 2, the image processing apparatus 100 is connected to a data server 200, the operation unit 110, and the display unit 120.

The data server 200 stores three-dimensional tomographic images (volume data, three-dimensional image data, (hereinafter referred to as three-dimensional images)) obtained in advance by imaging a subject using an X-ray CT apparatus. It is assumed that each three-dimensional tomographic image is configured as a set of two-dimensional tomographic images (two-dimensional image data), and the position and orientation of each two-dimensional tomographic image are stored in the data server 200 after being converted into an expression in a reference coordinate system (a coordinate system in a space with reference to the subject). The three-dimensional image expressed in the reference coordinate system is input to the image processing apparatus 100 via the image acquisition unit 210.

The operation unit 110 receives an input of an operation of a mouse or a keyboard by a user, and inputs a parameter of the projection process to the image projection unit 212 and the image processing unit 213 via the parameter acquisition unit 211.

The display unit 120 displays a display image generated by the image processing apparatus 100. The display image is a two-dimensional image that can be displayed on the display unit 120. The display image is generated via a projection process or image processing. The display unit 120 also displays a GUI (Graphical User Interface) for acquiring an instruction given by the user.

The image processing apparatus 100 includes elements described below. The image acquisition unit 210 acquires a three-dimensional image (an original image) that is to be input to the image processing apparatus 100. The parameter acquisition unit 211 acquires a parameter related to the projection processing according to the instruction issued by the user and received by the operation unit 110. The image projection unit 212 acquires the parameters related to the projection process from the parameter acquisition unit 211, and projects the original image based on the acquired parameters thereby determining a two-dimensional projection image. That is, the image projection unit 212 corresponds to an example of projection unit configured to generate first two-dimensional image data by applying the projection process to three-dimensional image data. The image processing unit 213 acquires a parameter related to the projection process from the parameter acquisition unit 211, and calculates a parameter related to the image processing based on the acquired parameter. The image processing unit 213 then performs the image processing on the two-dimensional projection image based on the calculated parameter related to the image processing thereby determining a processed two-dimensional projection image. That is, the image processing unit 213 corresponds to an example of acquisition unit configured to acquire the second parameter related to the image processing based on the first parameter related to the projection processing. Furthermore, the image processing unit 213 also corresponds to an example of image processing unit configured to generate second two-dimensional image data by applying the image processing to the first two-dimensional image data using the second parameter. The display control unit 106 performs control such that the processed two-dimensional projection image is displayed on the display unit 120.

The image acquisition unit 210, the parameter acquisition unit 211, the image projection unit 212, and the image processing unit 213, which are elements described above, are functional units realized by the control unit 101 by executing programs stored in the storage unit 104. In a case where the image processing apparatus 100 does not include the display control unit 106, the display control unit 106 may also be realized, as one of functional units, by the control unit 101 by executing a program stored in the storage unit 104.

The above-described functional configuration is merely an example. A plurality of functional units may be configured into one functional unit. Conversely, one functional unit may be divided into a plurality of functional units.

Figure 3:
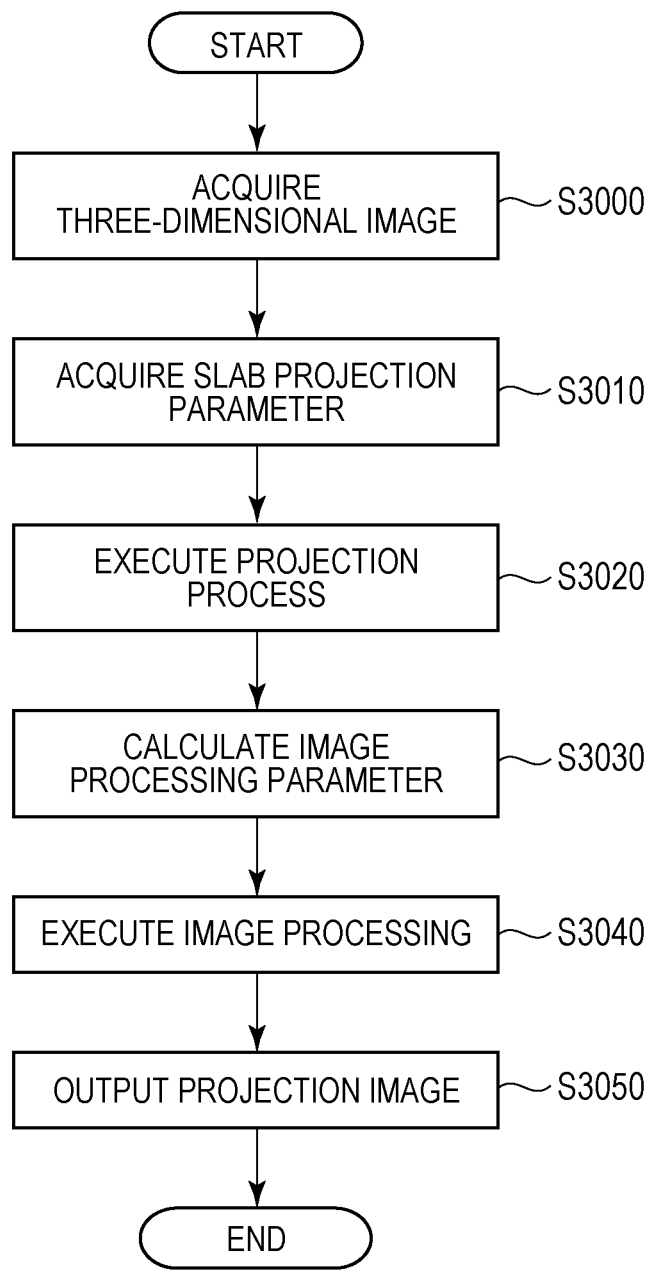
FIG. 3 is a flowchart illustrating an overall processing procedure according to the first embodiment.

FIG. 3 is a flowchart illustrating an example of an overall processing procedure performed by the image processing apparatus 100.

S3000: Acquiring Three-Dimensional Image

In step S3000, the image acquisition unit 210 acquires a three-dimensional image of a subject from the data server 200. The image acquisition unit 210 outputs the acquired three-dimensional image to the image projection unit 212. In the present embodiment, the image acquisition unit 210 acquires a three-dimensional image from the data server 200. However, in a case where the three-dimensional image is stored in the storage unit 104 in advance, the image acquisition unit 210 may acquire the three-dimensional image stored in the storage unit 104. Alternatively, the image processing apparatus 100 may read a three-dimensional image from a storage medium thereby acquiring the three-dimensional image. Alternatively, a set of two-dimensional tomographic images from which a three-dimensional image can be formed may be stored in the data server 200, and the image acquisition unit 210 may acquire the set of two-dimensional tomographic images from the data server 200 and may generate a three-dimensional image using these acquired two-dimensional tomographic images.

S3010: Acquiring Slab Projection Parameters

In step S3010, the parameter acquisition unit 211 acquires slab projection parameters according to an instruction given by a user. In the present embodiment, the parameters related to the slab projection (hereinafter referred to as slab projection parameters) include following three types: a projection direction vector, a thickness of a projection range (a slab thickness, a first parameter), and center position coordinates of the projection range. Although these three types of slab projection parameters are used in the present embodiment, slab projection parameters are not limited thereto.

An example of a method of acquiring slab projection parameters are described below. It is assumed that one slice image of the three-dimensional image acquired in step S3000 is now displayed on the display unit 120. It is assumed that the display image indicating the slice image can be changed to a cross-sectional image at an arbitrary position and an angle in accordance with an instruction given by the user. The user searches for a position that is the center of projection calculation while moving, scaling, and rotating the slice. When the position of the center of the projection calculation is determined, the slab thickness is input in a text box displayed on the display unit 120. For example, a value such as 3.0 mm is input. As a result of this operation, a direction orthogonal to a currently displayed slice at an arbitrary cross section is set as the projection direction vector, and coordinates of the center position of the currently displayed display image are set as the center position coordinates of the projection range. Furthermore, the value input in the text box is set as the slab thickness. These values are input to the image processing apparatus 100 as slab projection parameters.

S3020: Executing Projection Process

In step S3020, the image projection unit 212 performs an image projection process using the slab projection parameters (3 types: the projection direction vector, the projection range thickness (the slab thickness), and coordinates of the center of the projection range) acquired in step S3010 thereby calculating a projection image. As described above, in the present embodiment, the RaySum projection, which is a known projection method, is used in the image projection.

The RaySum projection is described below for a case where a slab thickness is used. In the projection process using a slab thickness, a limited region of the three-dimensional image is subjected to the projection process, unlike normal projection processes in which an entire region in a three-dimensional image is subjected to a calculation of the projection process. That is, a position defined by "center coordinates of the projection range", which is one of the slab projection parameters, is used as the starting point of the projection calculation, and a range of "±slab thickness/2" with respect to the projection calculation start position along the slab projection direction vector is set as the calculation range of the projection processing. This makes it possible to limit the range subjected to the calculation of the projection process to a region of interest.

The projection process has been described above by way of example for the case where the process is performed on a three-dimensional image (an original image) acquired by the image acquisition unit 210. However, the image processing may be performed in advance on the original image before the projection process is performed. For example, a noise removal process or a lump structure enhancement process may be performed as the image processing. This makes it possible to achieve an image noise reduction, three-dimensional lump structure enhancement, and/or the like, which may be difficult to achieve by performing the image processing on the projection image.

S3030: Calculating Image Processing Parameters

In step S3030, the image processing unit 213 calculates image processing parameters based on the slab projection parameters acquired in step S3010. In this step, of three types of slab projection parameters, the slab thickness is used.

Prior to the description of the image processing parameters calculated in this step, the image processing applied according to the present embodiment is described briefly. A further detailed description will be given later when step S3040 is described.

The image processing applied in this embodiment is a sharpening process. The sharpening process is represented by an equation described below.

$$I'(x,y)=I(x,y)+\alpha \times S(x,y) \qquad (1)$$

Equation (1) represents a density value obtained at a coordinate position (x, y) in the projection image after the sharpening process is performed. I(x, y) represents a density value at coordinates (x, y) of the projection image before the sharpening process is performed, S(x, y) represents a density value at coordinates (x, y) of an edge component image, and α represents a weighting factor of the edge component image. This equation indicates that the edge component image is added to the original image with the constant weight α.

The parameter to be subjected to the present step is α (the weighting factor of the edge component image) in equation (1). In the present embodiment, when the slab thickness is larger than a particular value (10.0 mm in this example), α is set to 1.5, while when the slab thickness is smaller than or equal to the particular value, α is set to 0.0. That is, when the slab thickness is smaller than or equal to the particular value, sharpening is not performed. Although α is set to 0.0 when the slab thickness is smaller than or equal to the particular in the present embodiment, any value may be employed as long as the employed value does not cause the sharpening process to convert the image to an unnatural image including enhanced noise. For example, a value very close to 0, such as α=0.0001 may be employed in the sharpening process.

In the present embodiment, a threshold value is set to 10.0 mm at which switching occurs as to whether the sharpening process is performed or not. This value is merely an example, and the value may be changed to another value according to the subject and/or the image. Furthermore, the parameter value (α=1.5) of the sharpening process is also merely an example, and can be changed to another value according to the subject and/or the image.

Furthermore, in the present embodiment, an example has been described in which the switching is performed according to the slab thickness as to whether the sharpening process is performed or not. However, alternatively, the parameter value of the sharpening process may be continuously changed according to the slab thickness. In this case, α may be set to 0.0 when the slab thickness is equal to a value (for example, 5.0 mm), and α may be set to 2.0 when the slab thickness is equal to another value (for example, 15.0 mm). In a range of the slab thickness between 5.0 mm and 15.0 mm, α is given by linear interpolation between the two values described above. This makes it possible to effectively correct a reduction in sharpness in a projection image due to an increase in slab thickness.

S3040: Executing Image Processing

In step S3040, using the image processing parameters calculated in step S3030, the image processing unit 213 performs image processing on the projection image calculated in step S3020.

Figure 4:
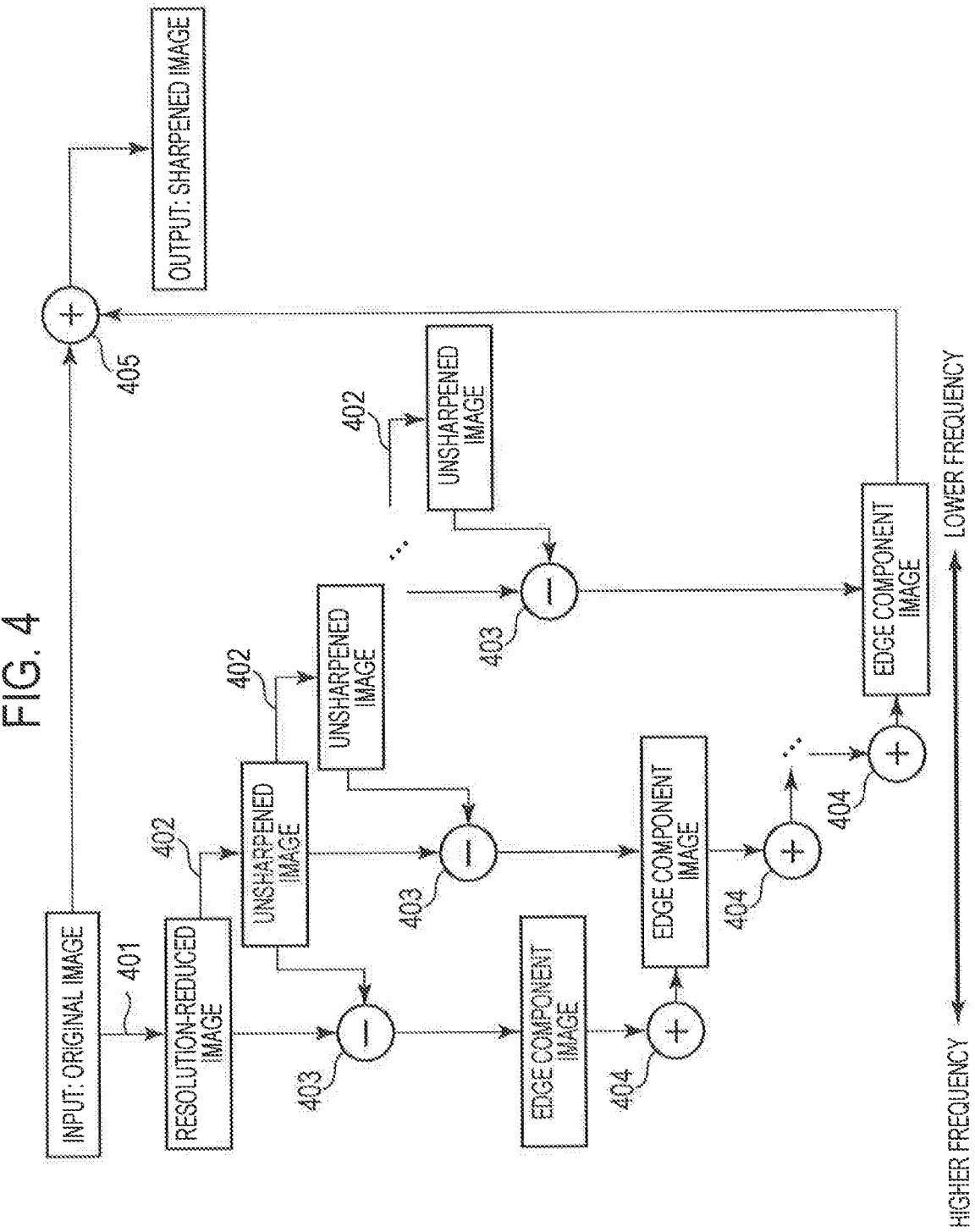
FIG. 4 is a schematic diagram illustrating an algorithm of a sharpening process according to the first embodiment.

The image processing according to the present embodiment is described in detail below with reference to FIG. 4. As described above in the description of step S3030, in the present embodiment, the sharpening processing is performed as the image processing. In this sharpening process, a multi-resolution sharpening process disclosed in "Present and Future of Breast Imaging Technology: Image Processing Techniques in Mammography" (Fujita, Journal of the Society of Photography and Imaging of Japan, Vol. 69, No. 1, 16-22, 2006) is applied to a breast CT image treated in the present embodiment. In the present embodiment, the sharpening process includes following five sub-processes: an image resolution reduction (401), a conversion to an unsharp image (402), subtracting an image 2 from an image 1 (403), adding the image 2 to the image 1 with a weight (404), and adding an edge component image to an original image with a weight (405).

The process performed in step S3030 according to equation (1) corresponds to the process of adding the edge component image to the original image (405). That is, the parameter (the second parameter) calculated in step S3030 corresponds to the value of the weight used in the weighted addition process of the edge component image.

The procedure of the sharpening process is as follows. First, the resolution reduction process (401) is applied to the original image to obtain an image in which the resolution in each axial direction is reduced by one half. Next, a plurality of unsharp images (blurred images) having different degrees of smoothness are generated by applying, a plurality of times, a conversion process (402) to the unsharp images to the reduced-resolution images. This process is realized by using a known smoothing filter process such as a Binomial filter process. By determining the difference between the unsharp images adjacent in smoothness to each other (that is, close in smoothness) obtained in the above-described manner (403), edge images which are different in fineness are obtained. Edge images obtained by the difference between images having small smoothness (that is, images obtained by applying, a small number of times, the process to convert images to unsharpened images (402)) corresponds to an edge in a high-frequency region, while a result obtained by the difference between images which are large in degree of smoothness corresponds to an edge in a low-frequency region. Thereafter, all the edge component images are added together by a weighted addition process (404). Finally, the resultant added edge component image is added to the original image (405) with a weight to obtain a sharpened image.

The sharpening method according to the present embodiment is different from that disclosed in "Present and Future of Breast Imaging Technology: Image Processing Techniques in Mammography" (Fujita, Journal of the Society of Photography and Imaging of Japan, Vol. 69, No. 1, 16-22, 2006) in that the method according to the present embodiment includes a resolution-reduction process (401) performed on an original image. This difference originates from a fact that voxel sizes of breast CT images treated in the present embodiment are as small as about 0.1 mm$^3$. Edges that are to be emphasized by the sharpening process exist in relatively low-frequency regions. However, since the voxel size in the original image is small. Therefore, to cover a low frequency region in a multi-stage smoothing process, it is necessary to increase the number of stages or the amount of smoothing per stage. Increasing the number of stages results in an increase in the amount of calculation, and may adversely affect the response in observing images. To handle the above situation, in the present embodiment, the resolution is reduced in advance thereby increasing the smoothing amount per stage without increasing the calculation amount.

The sharpening process described above further includes other parameters to be adjusted. They are a parameter that determines "the number of stages" and a parameter that determines "the weight adding edge component images at each stage". In the present embodiment, there are four allowable resolutions, and weights 0.6, 0.6, 0.8, and 1.0 which are allowed to be employed as weights in adding together different-stage edge images in order from the highest frequency to lower frequency. Note that these set values are merely examples, and values may be changed depending on characteristics of the subject. In a case where the voxel size of the original image is relatively large and thus it is possible to calculate the edge components in the low frequency region without performing the resolution conversion, the resolution reduction process (401) may not be performed.

S3050: Outputting Projection Image

In step S3050, the display control unit 106 performs control to display the image-processed projection image calculated in step S3040 on the display unit 120.

The process performed by the image processing apparatus 100 has been described above.

According to the present embodiment, even when the slab thickness is increased in the RaySum projection process, it is possible to calculate a sharp projection image with corrected blur, which allows a doctor to easily interpret the image.

First Modification of First Embodiment

The first embodiment has been described above by way of example for the case in which the image processing (the sharpening process) is performed when the slab thickness in the projection display is larger than the particular value, but the image processing is not performed when the slab thickness is equal to or less than the particular value. Note that the process is not limited to the example described above. For example, whether the image processing is performed or not may be switched depending on whether projection displaying is performed or not. For example, when the projection displaying is not performed, the image processing may not be performed, while when the projection displaying is performed, the image processing may be performed regardless of the slab thickness. In this case, the determination as to whether to perform the projection displaying may be made depending on whether a specific pattern of the luminance distribution (texture) is detected or not. For example, in the case of a breast CT image, when a particular region has a high luminance and has a small variation in the luminance compared to a surrounding region, there is a high possibility that this particular region is a tumor region. In view of the above, when a region of interest being observed has such a feature, it is determined that projection displaying is performed, but otherwise, it is determined that projection displaying is not performed. Instead of switching whether the image processing is performed or not in accordance with the whether the projection displaying is performed or not, an instruction issued by a user may be acquired and the determination as to whether the image processing is to be performed or not may be determined according to the instruction.

In this case, in the condition determination as to whether or not to perform the image processing, it becomes unnecessary to have prior knowledge such as that when the slab thickness is larger than a specific value (in mm), if the image processing is performed, it is possible to obtain a projection image which is easy to observe. Therefore, the technology according to the present embodiment can be applied regardless of the type of the subject.

The above process corresponds to an example of a process performed by the determination unit configured to determine that the image processing is to be performed when projection process is performed, while the image processing is not to be performed when the projection process is not performed, and corresponds to an example of a process performed by the image processing unit configured to execute the image processing based on a result of the determination made by the determination unit.

Second Modification of First Embodiment

In the first embodiment described above, the description has been given by way of example for the case where only the information related to the slab thickness is used in the calculation of the image processing parameters. However, the image processing parameters may be calculated taking into account the information related to the subject in addition to the slab thickness. For example, in a case where a breast CT image is observed, image processing parameters may be adjusted according to information indicating whether the density of the mammary gland is high or low. More specifically, in the case where the density of the mammary gland is high, the weight of the sharpening process is set to be, for example, twice as large as in the case where the density of the mammary gland is low.

In this situation, since the image processing parameters can be adjusted according to the characteristics of the subject in addition to the slab thickness, it is possible to perform more suitable image processing for individual images.

Third Modification of First Embodiment

In the first embodiment described above, the description has been given by way of example for the case where only the information related to the slab thickness is used in the calculation of the image processing parameters. The second modification of the first embodiment has been given by way of example for the case where the information related to the slab thickness and the information related to the subject are used in the calculation of the image processing parameters. These two modes described above may be switched as necessary. For example, in accordance with an instruction given by a user, the process may be switched between the process of determining the image processing parameters based on only the slab thickness (as in the first embodiment), and the process of determining the parameters based on the subject information and the slab thickness (as in the second modification of the first embodiment). That is, this corresponds to an example of a process performed by the image processing unit configured to select at least one second parameter from among a plurality of acquired second parameters.

In a case where in the observation of an image of a subject, the image is compared with an image of another subject or an image of the same subject captured at another different time, the image processing parameters may be determined based on only the slab thickness, which allows it to observe the images under the same conditions. On the other hand, in a case where only one image is observed, the image processing parameters may be calculated taking into account both the slab thickness and the subject information thereby making it possible to perform the image processing in a more optimum manner. According to the present modification, as described above, it is possible to provide a better image optimized according to the observation conditions.

Fourth Modification of First Embodiment

In the first embodiment described above, the description has been given by way of example for the case where the image processing performed by the image processing unit 213 is the sharpening process. However, other processing may be performed in the image processing. For example, a dynamic range compression technique may be employed as the image processing. A specific example is described below flow the case where a technique disclosed in "Development of Dynamic Range Compression Technique for Digital X-Ray Images" (Nakazawa et al., Konica Technical Report, Vol. 9, 35-40, 1996) is employed.

The dynamic range compression is an image processing in which density values of an image are converted so as to reduce the difference (the dynamic range) between a brightest density value and a darkest density value in the image. The dynamic range compression is effective when it is desired to improve the visibility of a dark region in an image while maintaining the gradation in a bright region in the image. Let it be assumed here, for example, that there is an image including a tumor region having a high density value (that is, bright) and a fat region having a low density value (that is, dark). In this situation, if the window width and the window level (WW/WL) are adjusted so that the gradation in the tumor region can be observed, then most of the density values in the fat region are below the lower limit value of the window level, and thus the fat region is completely blackened. In such a situation, if the dynamic range compression is applied, density values in the low-density region are increased and density values in the high-density region is reduced, and thus it becomes possible to observe the gradation both in the tumor region and in the fat region simultaneously.

In this situation, if a change in the projection image occurs as a result of changing the slab thickness, it is necessary to change the dynamic range compression parameter (the second parameter) accordingly. For example, when the slab thickness is small (for example, such as about 5.0 mm), the gradation in the tumor and the gradation in the fat region can be simultaneously observed without performing the dynamic range compression. On the other hand, when the slab thickness is large (for example, about 15.0 mm), the contrast in the tumor is reduced by averaging the density values by the RaySum projection. If WW/WL is adjusted to make it possible to visually recognize the small contrast, there is a possibility that the fat area is completely blackened and thus the dynamic range compression is required. Note that if the parameters of the dynamic range compression are not inappropriate, there is a possibility that a reduction in the visibility occurs against the intention. To handle the above situation, in the present modification, the parameters of the dynamic range compression are changed according to the slab thickness.

Figure 5:
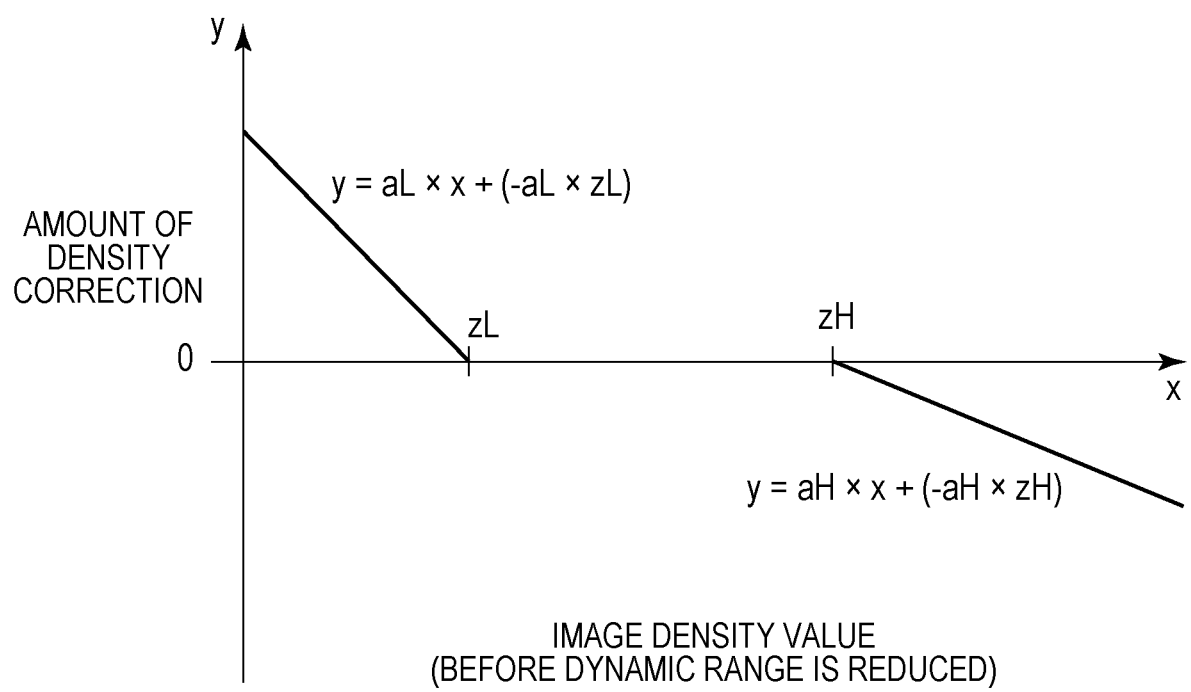
FIG. 5 is a schematic diagram illustrating an algorithm of a dynamic range compression process according to a fourth modification of the first embodiment.

The parameters of the dynamic range compression are described below with reference to FIG. 5. The dynamic range compression is realized by converting the density values of all voxels in an image using a function shown in FIG. 5. In FIG. 5, a horizontal axis x represents the image density value as of before the application of the dynamic range compression, and a vertical axis y represents the density value correction amount. The parameters to be adjusted are following four parameters: ZL; ZH; aL; and aH. ZL and ZH are threshold values that define a density value range within which the density values are subjected to the conversion. Density values equal to or lower than ZL are to be increased, while density values equal to or higher than ZH are to be reduced. aL and aH are coefficients of a linear function for calculating the correction amount, where aL is related to the increasing in a low density range and aH is related to the reduction in a high density range. By adjusting these four parameters in the above-described manner, it is possible to change the effect of the dynamic range compression.

In the present modification, when the slab thickness is equal to or less than a particular value (10.0 mm), the dynamic range compression is not performed (that is, ZL, ZH, aL, and aH are all set to 0), while when the slab thickness is larger than the particular value, the parameters are set such that ZL=−600, ZH=−200, aL=−0.5, and aH=−0.5. Although in the present modification, when the slab thickness is equal to or smaller than the particular value, all of ZL, ZH, aL, and aH are set to 0, the parameters may be set to arbitrary values as long as the visibility is not reduced. For example, the dynamic range compression may be performed by setting all of ZL, ZH, aL, and aH to values infinitely close to 0, such as 0.0001.

Although the threshold value of the slab thickness is set to 10.0 mm at which switching occurs at to whether the dynamic range compression processing is applied or not, this value is merely an example, and the value may be changed to another value according to the subject and/or the image. Furthermore, the parameter values are merely examples, and the parameter values may be changed to other suitable values according to the subject and the image.

In the above-described example, the dynamic range compression process is applied or not depending on the slab thickness. Alternatively, the parameter values may be continuously changed according to the slab thickness. In this case, when the slab thickness is equal to a particular value (for example, 5.0 mm), aL and aH are set to −0.0, while when the slab thickness is equal to another value (for example, 15.0 mm), aL and aH are set to −0.5. In a range of the slab thickness between 5.0 mm and 15.0 mm, c is given by linear interpolation between the two values described above. By setting the parameter values in the above-described manner, it is possible to effectively correct a decrease in contrast in a projection image due to an increase in slab thickness.

According to the present modification, even when WL/WW is adjusted such that the gradation in a tumor can be observed for a large slab thickness, the parameters of the dynamic range compression are appropriately adjusted, and the good visibility of the region of interest can be maintained.

Fifth Modification of First Embodiment

In the first embodiment described above, the description has been given by way of example for the case where the RaySum projection is employed as the projection method and the sharpening process is performed as the image processing. However, a projection method or an image processing method different from those used in the first embodiment may be used. An example is described below in which a maximum intensity projection (MIP) is used as the projection method.

As described above, the RaySum projection is a projection method suitable mainly for observing properties of a tumor region, such as a manner in which a contour of the tumor region or a surrounding tissue are drawn into the tumor. In contrast, the MIP is a projection method suitable to display, in an emphasized manner, a calcified region, which is a minute high-density region (a high-density isolated point region) distributed in the form of an isolated point group.

Observation of a calcified region using MIP also has a problem that occurs with a change in slab thickness, as in the case of RaySum projection. When the slab thickness is small (that is, the projection range is small), the number of calcified regions existing in the projection range is small. Therefore, to observe all calcified regions existing in the whole subject, it is necessary to see a large number of images while moving a slice. However, it is possible to obtain a high contrast to regions surrounding the calcified regions is obtained, and the high visibility is obtained in the observation. On the other hand, when the slab thickness is large (that is, the projection range is large), more calcified regions can be displayed at a time. However, the difference in contrast between the calcified regions and the surrounding regions is small, and thus the calcified regions are buried in the surrounding tissue and are difficult to observe.

In the present modification, in order to solve the above-described problem, a calcified region enhancement process is performed as the image processing. The degree of enhancement is changed according to the slab thickness. As described above, the calcified regions are high density regions existing in the form of isolated points. Therefore, the calcified regions can be detected by applying a known corner detection method such as a Harris operator. The density values in the detected calcified regions are multiplied by a constant enhancement factor thereby generating an image in which the calcified regions are emphasized. In this case, the enhancement factor is a parameter to be adjusted according to the slab thickness.

In the present modification, when the slab thickness is equal to or smaller than a particular fixed value (for example, 10.0 mm), the calcified region enhancement process is not performed (that is, the enhancement factor is set to 1.0), while when the thickness is larger than the particular fixed value, the calcified region enhancement process is performed (that is, the enhancement factor is set to 2.0). In this way, in the MIP, the image processing parameter is adjusted. In the present modification, the enhancement factor is set to 1.0 when the slab thickness is equal to or less than the particular value. However, the enhancement factor may be set to an arbitrary value as long as the calcified regions are not buried in the surrounding tissue in the MIP image. For example, a value very close to 1.0, such as 1.0001 may be employed as the enhancement factor in the MIP process.

The present modification has been described above by way of example for the case where MIP is used as the projection method. However, other projection methods may be employed. For example, minimum intensity projection (MinIP) may be employed as the projection method. This projection method is described below by way of example for the case where a three-dimensional chest CT image is treated. MinIP is a projection method suitable for observing a lung region having a low CT value in a chest CT image, because a minimum density value on a projection path is reflected in the projection image. A tumor region is displayed with a further lower CT value than in surrounding normal regions. Increasing the slab thickness may result in a reduction in the difference in contrast between the tumor region and the normal region in the MinIP image. In this case, first, the tumor region is extracted from a three-dimensional image (an original image) by applying a known filter such as a lump structure extraction filter. When the slab thickness is larger than a particular value (for example, 10.0 mm), image processing is performed on the MinIP image to reduce CT values in the tumor region. In this way, in the MinIP, the image processing parameter is adjusted.

Sixth Modification of First Embodiment

In the first embodiment and the first to fifth modifications, descriptions thereof have been given by way of example for the case where the image processing performed by the image processing unit 213 is a single image processing such as a sharpening process or a dynamic range compression process. However, the image processing performed by the image processing unit 213 may be a combination of a plurality of processes. For example, the sharpening process is performed first and then the dynamic range compression process may be performed, or these processes may be performed in a reverse order. In this case, the execution order of the processes in the image processing may be determined (calculated) based on the contrast in the projection image. When the contrast of the projection image in the state in which no image processing is yet performed is high, if the sharpening process is performed first, edges may be excessively emphasized. In such a case, first, the contrast of the projection image is reduced by performing the dynamic range compression process, and then the sharpening process is performed. The contrast of the projected image can be quantitatively calculated by using a known contrast calculation method such as a Michelson contrast calculation method. When the contrast value is equal to or greater than a particular fixed value (for example, 0.5), the dynamic range compression processing is performed first, while when the contrast value is smaller than the particular fixed value, the sharpening process is performed first. Thereafter, control is performed to display a two-dimensional image (a third two-dimensional image) obtained by applying the image processing in the above order on the display unit 120. Thus, it becomes possible to perform an effective correction that is difficult to be achieved by only a single image processing.

Seventh Modification of First Embodiment

In the first embodiment and the first to sixth modifications, descriptions thereof have been given by way of example for the case where when the slab thickness is small, image processing parameters are calculated based on the slab thickness such that the image processing is not performed. Note that when the slab thickness is small, the image processing may be skipped without calculating the image processing parameters. In a seventh modification, processing is performed as described below with reference to FIG. 6.

Figure 6:
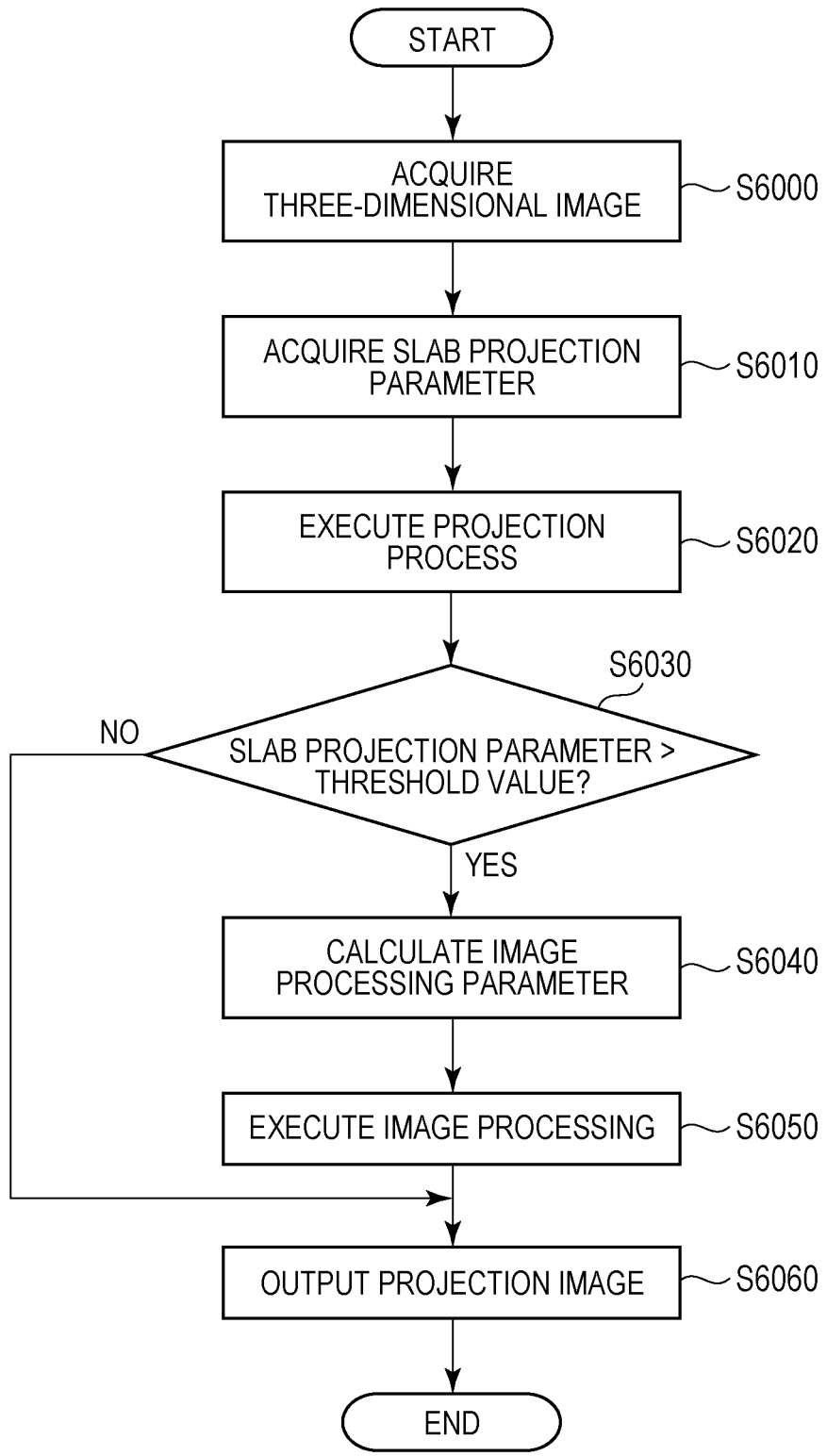
FIG. 6 is a flowchart illustrating an overall processing procedure according to a seventh modification of the first embodiment.

FIG. 6 is a flowchart illustrating an example of an overall processing procedure performed by the image processing apparatus 100 according to the seventh modification. Steps S6000 to S6020 and steps S6040 to S6060 are similar to steps S3000 to S3020 and steps S3030 to S3050 described above with reference to FIG. 2, and thus a description thereof is omitted.

S6030: Slab Projection Parameter>Threshold?

In step S6030, the image processing unit 213 determines whether or not the slab projection parameter acquired in step S6010 is larger than a threshold value. More specifically, it is determined whether or not a value of a slab projection parameter, which is included in slab projection parameters and indicates the slab thickness, is larger than a predetermined threshold value (for example, 10.0 mm). Note that, as in the first embodiment, the threshold value is merely an example, and may be changed to a suitable value according to the subject and the image.

In a case where the image processing unit 213 determines that the slab projection parameter is larger than the threshold value, the process proceeds to step S6040, and calculates the image processing parameter and executes the image processing as described above in the first embodiment. On the other hand, in a case where the image processing unit 213 determines that the slab projection parameter is not greater than the threshold value, that is, when it is determined that the slab projection parameter is equal to or smaller than the threshold value, the image processing unit 213 proceeds to step S6060 without executing steps S6040 and S6050.

By performing the steps in the manner described above, it becomes possible to, when the slab thickness is equal to or smaller than the particular fixed value, perform control such that the image processing is not executed without calculating the image processing parameter so as to cause the image processing not to be executed.

Eighth Modification of First Embodiment

In the first embodiment and the first to seventh modifications, the display control unit 106 performs control such that the display unit 120 displays a two-dimensional image obtained as a result of performing the image processing. A user may check the displayed two-dimensional image and may specify an image processing parameter, according to which the image processing unit 213 may re-execute the image processing. The display control unit 106 may display the re-executed result on the display unit 120. The display control unit 106 may perform control such that the display unit 120 switches the displayed image between the image subjected to the image processing and the image not subjected to the image processing in accordance with an instruction given by a user, or may perform control such that the images are displayed side by side. This makes it possible for the user to check a desired image processing result whatever parameters such as the slab thickness are.

Second Embodiment

In the first embodiment described above, the description has been given by way of example for the case where only the information related to the slab thickness is used in the calculation of the image processing parameters. In contrast, in a second embodiment described below, the image processing apparatus calculates image processing parameters based on a display mode in which the projection image is displayed. More specifically, the image processing parameters are changed between when the slice position of the projection image is moved back and forth in the observation (a slice position movement display mode) and when the center of rotation of the viewpoint position in a three-dimensional space is set at a certain position in the image and the viewpoint position is rotated in the observation (a rotation display mode). Note that it is assumed that the image processing is the sharpening process as in the first embodiment.

The manner and effects of changing the image processing parameters between the slice position movement display mode and the rotation display mode are described below for the case of a breast CT image as in the first embodiment. This is because the structure or feature to be focused on in the interpretation differs depending on the projection image display mode. The moving of the slice position in the projection image is performed when a fine structure is observed in detail. In this case, the slab thickness is reduced in the observation. In this case, if the sharpening process is performed, then the contrast becomes too high, which makes it difficult to observer the image. On the other hand, the displayed projection image is rotated when the entire three-dimensional shape of the region of interest such as a tumor region is grasped. In this case, the slab thickness is increased so as to make it possible to grasp the overall shape. In such a case, the sharpening process allows it to obtain an image which is easier to observe.

The hardware configuration of the image processing apparatus 100, the functional configuration of the image processing apparatus 100, and the system configuration of the image processing system according to the present embodiment are the same as those of the first embodiment (FIGS. 1 and 2). However, the processing contents of the parameter acquisition unit 211 and the image processing unit 213 are different.

The parameter acquisition unit 211 acquires parameters required by the image processing apparatus 100 in accordance with an instruction given by the user via the operation unit 110. In the present embodiment, information indicating the projection image display mode is acquired as a parameter in addition to the parameter relating to the projection process acquired in the first embodiment. The image processing unit 213 calculates image processing parameters based on the information indicating the projection image display mode acquired by the parameter acquisition unit 211. Then, the image processing is performed based on the calculated parameters thereby generating the processed projection image.

FIG. 7 is a flowchart illustrating an example of an overall processing procedure performed by the image processing apparatus 100 according to the present embodiment. Steps S7000 to S7010, step S7030, and steps S7050 to S7060 are the same as steps S3000 to S3010, S3020, and S3040 to S3050 shown in FIG. 3, and thus a description thereof is omitted.

S7020: Acquiring Projection Image Display Mode

In step S7020, the parameter acquisition unit 211 acquires information indicating the projection image display mode based on an instruction given by the user via the operation unit 110. As described above, the projection image display mode indicated by the information acquired according to the present embodiment is either "the slice position movement display mode" or "rotation display mode". For example, the display mode can be acquired using a GUI displayed on the display unit 120. More specifically, for example, a set of radio buttons described as "slice position movement display mode" and "rotation display mode" is displayed on the display unit 120, and the display mode indicated by the radio button selected by the user with a mouse or the like is acquired.

S7040: Calculating Image Processing Parameters

In step S7040, the image processing unit 213 calculates image processing parameters based on the projection image display mode indicated by the information acquired in step S7020. In the present embodiment, the parameters for the sharpening process are calculated. When the projection image display mode is "slice position movement display mode", the sharpening process is not performed (that is, the weight of the sharpening term is set to 0). On the other hand, when the projection image display mode is the "rotation display mode", the sharpening process is performed (that is, the weight of the sharpening term is set to 1.5 as in the first embodiment). When the projection image display mode is "slice position movement display mode", the sharpening process may be performed by setting the weight of the sharpening term to a value as close to 0 as possible. That is, these process are examples of a process performed by the determination unit configured to determine that the image processing is to be executed when the display mode is the rotation display mode and determine that the image processing is not to be executed when the display mode is the slice position movement display mode, and a process performed by the image processing unit configured to execute the image processing based on a result of the determination made by the determination unit.

The process performed by the image processing apparatus 100 has been described above.

According to the present embodiment, it is possible to calculate suitable image processing parameters depending on the display mode in which an image is observed, which makes it easy to perform image interpretation.

First Modification of Second Embodiment

In the second embodiment, the description has been given by way of example for the case where two display modes are provided, one of which is "slice position movement display mode" and the other one is "rotation display mode. However, other display modes may be employed. For example, the image processing parameters may be switched according to whether the projection direction is axial, sagittal, or coronal direction.

In this case, the image processing unit 213 acquires, in addition to the projection direction, a three-dimensional image of a subject from the image acquisition unit 210. Then, a calculation is performed to determine a projection distance in a state in which the three-dimensional image of the subject is projected in the projection direction. When the projection distance is larger than a particular value (for example, 10.0 mm), the sharpening process is performed, while when the projection distance is smaller than the particular value, the sharpening process is not performed. When the projection distance is the same as the particular value, the sharpening processing may or may not be performed. Thus, it is possible to provide a suitable image display according to the projection direction.

The above process is an example of a process performed by the determination unit configured to determine that image processing is executed when the projection distance of a subject in the display direction is larger than a particular value while the image processing is not executed when the projection distance is smaller than the particular value, and an example of a process performed by the image processing unit configured to execute the image processing based on a result of the determination made by the determination unit.

Furthermore, in MPR (Multi Planar Representation) display in which projection images in all projection directions of axial, sagittal, and coronal directions are simultaneously displayed, the image processing parameters may be changed for each display image. In this case, it is possible to generate a display image suitable for each projection direction.

Second Modification of Second Embodiment

In the second embodiment, the description thereof has been given by way of example for the case where the image processing parameters are determined only depending on the projection image display mode. That is, the image processing parameters are the same in the same projection image display mode. However, when the display mode is "rotation display mode", the image processing parameters may be changed in accordance with the rotation angle. The details of the process performed in this case is are described below.

In the present modification, the process in step S7040 for calculating the image processing parameters is as follows. First, the image processing unit 213 acquires the projection direction from the parameter acquisition unit 211. Then, the slab thickness is calculated based on the three-dimensional image of the subject and the projection direction. A method for calculating the slab thickness will be described in detail in the next paragraph. Then, using the same method as in step S3030 according to the first embodiment, the image processing unit 213 determines the image processing parameters based on the slab thickness.

Figure 8A:
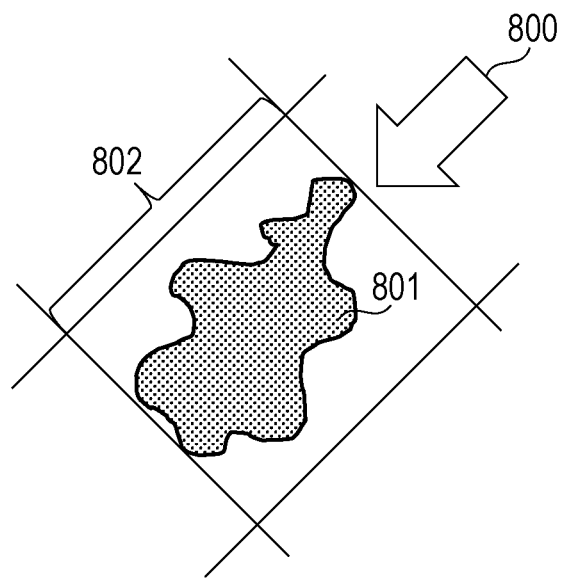
FIG. 8A is a schematic diagram illustrating an algorithm for calculating a slab thickness according to a second modification of the second embodiment.
Figure 8B:
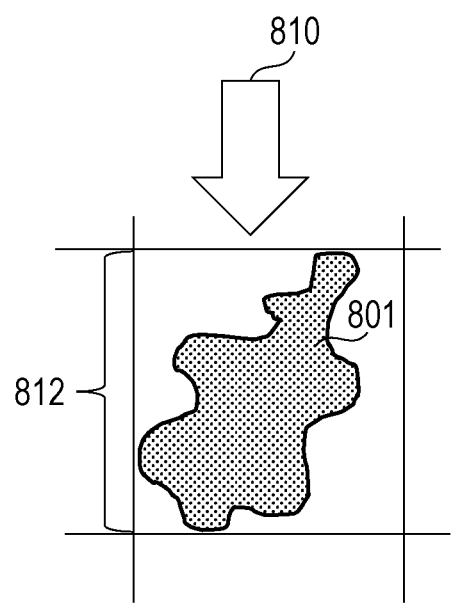
FIG. 8B is a schematic diagram illustrating an algorithm for calculating a slab thickness according to the second modification of the second embodiment.

A method of calculating the slab thickness using the projection direction is described below with reference to FIGS. 8A and 8B. FIG. 8A is a schematic diagram illustrating a slab thickness when a subject image is projected. Here it is assumed that a part of interest (for example, a tumor region) 801 is projected in a direction indicated by an arrow 800 and the projected image is displayed. In this case, the thickness of the slab that includes the part of interest necessarily and sufficiently is the thickness indicated by 802. Therefore, in this case, the slab thickness is set to the thickness indicated by 802. Next, let it be assumed that the projection direction is changed such that the projection is performed in the direction shown by an arrow 810 as shown in FIG. 8B. Here, it should be noted that the angle of the region of interest 801 of the subject has not changed. In this case, the thickness of the slab that includes the part of interest necessarily and sufficiently is the thickness indicated by 812. That is, the thickness of the slab is set to include the part of interest necessarily and sufficiently, and the thickness of the slab changes depending on the projection direction. In the present modification, the slab thickness including the region of interest as necessary and sufficient is calculated and set according to the projection direction.

In this case, the image processing parameters are automatically calculated according to the projection direction. When the projection length of the region of interest is long (that is, thick) in the projection direction in which the observation is currently performed, the calculated slab thickness is also large. In step S3030 in the first embodiment, when the slab thickness is large, the effect of the image processing (the sharpening processing) is enhanced. On the other hand, when the projection length of the region of interest in the projection direction in which the observation is currently performed is small (that is, thin), the calculated slab thickness is also small, and the effect of the image processing (the sharpening processing) is weakened. In a case where the RaySum projection is used as the image projection algorithm, the longer the projection length, the more the image tends to blur. According to the present modification, it is possible to effectively correct a blur caused by an increase in the projection length.

Third Modification of Second Embodiment

In the second embodiment, the description has been given by way of example for the case in which, when the projection image display mode is "slice position movement display mode", the image processing parameters are calculated so as to cause the image processing not to be performed. However, when the projection image display mode is "slice position movement display mode", the image processing may be skipped without calculating the image processing parameters in a similar manner to the seventh modification of the first embodiment. In this case, the process according to the third modification of the second embodiment is performed as described below with reference to FIG. 9.

FIG. 9 is a flowchart illustrating an example of an overall processing procedure performed by the image processing apparatus 100 according to the present modification. Steps S9000 to S9030 and steps S9050 to S9070 are the same as steps S7000 to S7030 and steps S7040 to S7060 in FIG. 7, and thus a description thereof is omitted.

S9040: Projection Image Display Mode=Rotation Display Mode?

In step S9040, the image processing unit 213 determines whether the information indicating the projection image display mode acquired in step S9020 indicates "rotation display mode" or not ("slice position movement display mode). In a case where the image processing unit 213 determines that the information indicating the projection image display mode indicates "rotation display mode", the process proceeds to step S9050, and calculates the image processing parameters and executes the image processing as described in the second embodiment. On the other hand, in a case where the image processing unit 213 determines that the information indicating the projection image display mode is not "rotation display mode", that is, in a case where it is determined that the information indicating the projection image display mode indicates "slice position movement display mode", the process proceeds to step S9070. That is, steps S9050 and S9060 are not executed.

Thus, when the projection image display mode is "slice position movement display mode", it is possible to control not to execute the image processing without calculating image processing parameters that cause the image processing not to be executed.

Other Embodiments

The embodiments have been described above in detail. Note that the present invention can be implemented as a system, an apparatus, a method, a program, a storage medium, or the like. More specifically, for example, the present invention may be applied to a system including a plurality of devices among which the functions of the image processing apparatus are distributed. Conversely, the present invention may be applied to an apparatus including a single device. A function and/or a process according to the present invention may be realized on a computer by installing a program code on the computer thereby realizing the present invention. The computer program itself for realizing the functions and/or the processes disclosed in the above-described embodiments also falls within the scope of the present invention. The functions of the above-described embodiments are implemented by a computer by reading a program and executing it. Furthermore, a function of an embodiment may also be realized by performing an operation in cooperation with an OS or the like running on the computer based on an instruction of the program. In this case, the OS or the like performs part or all of the actual processing thereby realizing the functions of the above-described embodiments. Furthermore, the program read from a storage medium may be written into a memory provided in a function expansion board inserted in the computer or a function expansion unit connected to the computer, and some or all of the functions of the above-described embodiments may be realized. Note that the scope of the present invention is not limited by the above-described embodiments.

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

According to the present invention, the image processing can be applied to the first two-dimensional image data using the second parameter obtained based on the first parameter related to the projection process, and thus the three-dimensional image data can be projected into the two-dimensional image such that the region of interest is displayed in a high-visibility manner.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

What is claimed is:

1. An image processing apparatus comprising:
   a projection unit configured to generate first two-dimensional image data by applying a projection process to three-dimensional image data;

an acquisition unit configured to acquire a second parameter used in an image process based on a first parameter related to the projection process, wherein the first parameter includes at least information indicating a slab thickness in a projection direction of the projection process; and an image processing unit configured to generate second two-dimensional image data by applying the image process, including at least one of a sharpening process, a dynamic range compression process and a calcified region enhancement process, to the first two-dimensional image data using the second parameter in which an enhancement by the image process increases with an increase in the slab thickness in the projection direction of the projection process.

2. The image processing apparatus according to claim 1, further comprising
a determination unit configured to make a determination as to whether the image process is to be executed or not;
wherein the determination unit determines that the image process is to be executed in a case where the projection process is to be executed, the determination unit determines that the image process is not to be executed in a case where the projection process is not to be executed, and the image processing unit executes the image process based on a result of the determination made by the determination unit.

3. The image processing apparatus according to claim 1, wherein the first parameter includes at least information indicating a thickness in a projection direction in the projection process.

4. The image processing apparatus according to claim 1, wherein
the acquisition unit acquires a plurality of second parameters based on the first parameter, and
the image processing unit select at least one second parameter from the plurality of the acquired second parameters.

5. The image processing apparatus according to claim 1, wherein
the projection process is a ray summation projection process,
the image process is a sharpening process of sharpening the first two-dimensional image data by adding a weighted high-frequency component of the first two-dimensional image data to the first two-dimensional image data, and
the second parameter is a weight used in the adding the high-frequency component.

6. The image processing apparatus according to claim 1, wherein
the projection process is a ray summation projection process,
the image process is a dynamic range compression process,
the image process uses a plurality second parameters including a threshold value indicating a density value range within which the dynamic range compression process is performed, and a coefficient indicating a degree of the dynamic range compression process, wherein the degree of the dynamic range compression process is increased with increasing thickness in the projection direction in the projection process.

7. The image processing apparatus according to claim 1, wherein
the projection process is a maximum intensity projection process,
the image process is a process of enhancing a high-density isolated point region in the first two-dimensional image data,
the second parameter is a weight indicating a degree of enhancement of the high-density isolated point region,
the weight is increased with increasing thickness in the projection direction in the projection process.

8. The image processing apparatus according to claim 1, wherein
the image processing unit has two or more image processing methods, and
the image processing unit acquires an order of applying the two or more image processing methods, and generates third two-dimensional image data by applying the image process to the first two-dimensional image data according to the acquired order.

9. The image processing apparatus according to claim 1, wherein a parameter related to the projection process includes at least information indicating a display mode of displaying a two-dimensional image.

10. The image processing apparatus according to claim 9, further comprising
a determination unit configured to make a determination as to whether the image process is to be executed or not,
the display mode of displaying the two-dimensional image is allowed to be selected at least from following two modes: a slice position movement display mode; and
a rotation display mode,
wherein the determination unit determines that the image process is to be executed in a case where the display mode is a rotation display mode, the determination unit determines that the image process is not to be executed in a case where the display mode is a slice position movement display mode,
wherein the image processing unit executes the image process based on a result of the determination made by the determination unit.

11. The image processing apparatus according to claim 1, further comprising
a determination unit configured to make a determination as to whether the image process is to be executed or not
wherein the image processing unit calculates a projection distance at least in one of following display directions: an axial direction; a sagittal direction; and
a coronal direction,
wherein the determination unit determines that the image process is to be executed in a case where the projection distance of a subject in the display direction is greater than a predetermined value, the determination unit determines that the image process is not to be executed in a case where the projection distance is smaller than the predetermined value, and
wherein the image processing unit executes the image process based on a result of the determination made by the determination unit.

12. The image processing apparatus according to claim 1, wherein
the first parameter includes information indicating a shape of a subject in a region of interest, and
the acquisition unit calculates a projection length of the region of interest over an entire image region, sets the slab thickness in the projection direction in the projection process such that the slab thickness necessary and sufficiently includes the projection length, and calculates the at least one or more second parameters based on the slab thickness.

13. An image processing method comprising:

generating first two-dimensional image data by applying a projection process to three-dimensional image data;

acquiring a second parameter used in image process based on the first parameter of the projection process, wherein the first parameter includes at least information indicating a slab thickness in the projection process; and generating second two-dimensional image data by applying the image process, including at least one of a sharpening process, a dynamic range compression, and a calcified region enhancement process, to the first two-dimensional image data using the second parameter in which an enhancement by the image process increases with an increase in the slab thickness in the projection direction of the projection process.

14. A non-transitory computer-readable medium storing a program for causing a computer to execute the image processing method according to claim 13.

15. The image processing apparatus according to claim 1, wherein the image processing unit applies the image process to the first two-dimensional image data in a case where the first parameter related to the slab thickness in the projection process satisfies a predetermined condition.

16. The image processing apparatus according to claim 15, wherein one or more parameters are used as the parameter related to the projection process and the one or more parameters include at least information indicating a thickness in a projection direction in the projection process, and wherein the image processing unit applies the image process to the two-dimensional image data in a case where the slab thickness is smaller than the predetermined value, the image processing unit does not apply the image process to the two-dimensional image data in a case where the slab thickness is larger than a predetermined value.

17. The image processing apparatus according to claim 15, wherein the acquisition unit is configured to acquire a parameter related to the image process based on a parameter related to the projection process, wherein the image processing unit applies the image process to the two-dimensional image data using the parameter related to the image process.

18. The image processing apparatus according to claim 15, wherein in a case where the first parameter related to the projection process does not satisfy the predetermined condition, the acquisition unit acquires, as the parameter related to the image process, a value that causes the image process not to be applied to the two-dimensional image data.

19. The image processing apparatus according to claim 17, wherein the image process is a sharpening process of sharpening the two-dimensional image data by adding a weighted high-frequency component of the two-dimensional image data to the two-dimensional image data, and wherein the parameter related to the image process is a weight used in the addition of the high-frequency component.

20. The image processing apparatus according to claim 15, wherein the projection process is a sum value projection process.

21. The image processing apparatus according to claim 15, further comprising display control unit configured to perform control to display the second two-dimensional image data which has been subjected to the image process on a display unit in a case where the first parameter related to the projection process satisfies a predetermined condition, the display control unit performs control to display the second two-dimensional image data which is not subjected to the image process on the display unit in a case where the first parameter related to the projection process does not satisfy the predetermined condition.

22. The image processing method according to claim 13, further comprising:

performing image process to the first two-dimensional image data in a case where the first parameter related to the slab thickness in the projection process satisfies a predetermined condition.

23. A non-transitory computer-readable medium storing a program for causing a computer to execute the image processing method according to claim 22.

24. The image processing apparatus according to claim 1, wherein in a case that the slab thickness in the projection direction of the projection process is thicker than a predetermined thickness, the dynamic range compression process is applied onto the first two-dimensional image data, and in a case that the slab thickness in the projection direction of the projection process is equal to or thinner than a predetermined thickness, the dynamic range compression process is not applied onto the first two-dimensional image data.

25. The image processing apparatus according to claim 1, wherein in a case that the slab thickness in the projection direction of the projection process is thicker than a predetermined thickness, the sharpening process is applied onto the first two-dimensional image data, and in a case that the slab thickness in the projection direction of the projection process is equal to or thinner than a predetermined thickness, the sharpening process is not applied onto the first two-dimensional image data.

26. The image processing apparatus according to claim 1, wherein in a case that the slab thickness in the projection direction of the projection process is thicker than a predetermined thickness, the calcified region enhancement process is applied onto the first two-dimensional image data, and in a case that the slab thickness in the projection direction of the projection process is equal to or thinner than a predetermined thickness, the calcified region enhancement process is not applied onto the first two-dimensional image data.

* * * * *